(12) United States Patent
Tan et al.

(10) Patent No.: US 7,678,873 B1
(45) Date of Patent: Mar. 16, 2010

(54) ACETYLENE-TERMINATED HYPERBRANCHED POLY(ARYLENE-ETHER-KETONE-IMIDES)

(75) Inventors: Loon-Seng Tan, Centerville, OH (US); David H. Wang, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 2 days.

(21) Appl. No.: 12/079,086

(22) Filed: Feb. 11, 2008

Related U.S. Application Data

(60) Provisional application No. 60/902,556, filed on Feb. 21, 2007.

(51) Int. Cl.
*C08G 8/02* (2006.01)
(52) U.S. Cl. .................................................. 528/128
(58) Field of Classification Search .................. 528/128
See application file for complete search history.

(56) References Cited

U.S. PATENT DOCUMENTS 6,313,185 B1 * 11/2001 Lau et al. ....................... 521/77

OTHER PUBLICATIONS

Wang et al. Polymer Preprints 2006, 47(1), 298-299.*
Wang et al. (Polymer Preprint Mar. 2005, 46 (1), 793-794).*

* cited by examiner

*Primary Examiner*—Randy Gulakowski
*Assistant Examiner*—Shane Fang
(74) *Attorney, Agent, or Firm*—AFMCLO/JAZ; Bart S. Hersko

(57) ABSTRACT

Novel ether-ketone-imide hyperbranched polymers with thermally reactive ethynyl endgroups were prepared from the corresponding $AB_2$ monomer and the respective benzophenone-based endcapping agents in one-pot fashion. The resulting polymer has repeating units of the formula:

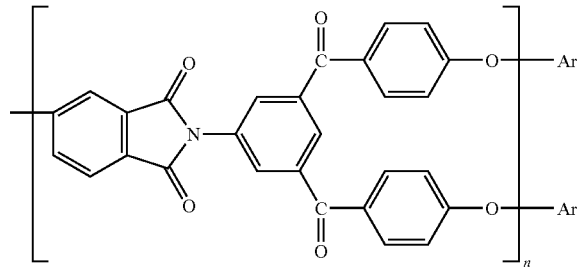

where the chain-end groups, Ar is a benzophenone with an ortho, a meta- or a para-ethynyl substituent.

4 Claims, No Drawings

ACETYLENE-TERMINATED HYPERBRANCHED POLY(ARYLENE-ETHER-KETONE-IMIDES)

CROSS REFERENCE TO RELATED APPLICATION

This application claims priority of the filing date of Provisional Application Ser. No. 60/902,556, filed on Feb. 21, 2007.

RIGHTS OF THE GOVERNMENT

The invention described herein may be manufactured and used by or for the Government of the United States for all governmental purposes without the payment of any royalty.

BACKGROUND OF THE INVENTION

The present invention relates to thermally reactive hyperbranched ether-ketone-imide polymers, particularly to those that are chain-end functionalized with acetylene (ethynyl) groups.

Dendritic macromolecules such as dendrimers and hyperbranched polymers are a class of highly branched polymers that have distinctly different properties from their linear analogs. Both dendrimers and hyperbranched polymers have much lower solution and melt viscosities than their linear analogs of similar molecular weights. They also have a large number of chain-ends whose collective influence dictates their overall physical and/or chemical behaviors. These features are attractive in terms of processability and offering flexibility in engineering required properties for specific applications. However, there is a practical advantage that hyperbranched polymers have over dendrimers at "raw material" level. Although dendrimers have precisely controlled structures (designated as generations), their preparations generally involve tedious, multi-step sequences that are impractical and costly in scale-up production. Synthesis of a hyperbranched polymer, on the other hand, is a one-pot process. Large quantities of hyperbranched polymers can be easily produced from $AB_x$ ($x \geq 2$) monomers. In some cases, the desired hyperbranched polymers can also be prepared from the polymerization of appropriate $A_2$ and $B_3$ or $A_3$ and $B_2$ monomers, where all these monomers are commercially available, thus obviating the added cost in the synthesis of $AB_2$ monomers.

Because of it non-entangling nature, hyperbranched polymers generally exhibit significantly lower solution and melt viscosities than their structurally similar linear counterparts. As such, various hyperbranched polymers have been used in lowering the melt viscosity in the processing of thermoplastics and thermosetting polymers.

Accordingly, it is an object of the present invention to provide thermally reactive, heat-resistant hyperbranched ether-ketone polymers containing ethynyl groups that can thermally self-polymerize to form cross-linked polymers.

It is another object of this invention to provide two new compositions for acetylenel-bearing endcapped, namely, 2'- and 3'-ethynyl-4-fluorobenzophenone. Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided new ether-ketone-imide hyperbranched polymers with the following repeating units of the formula:

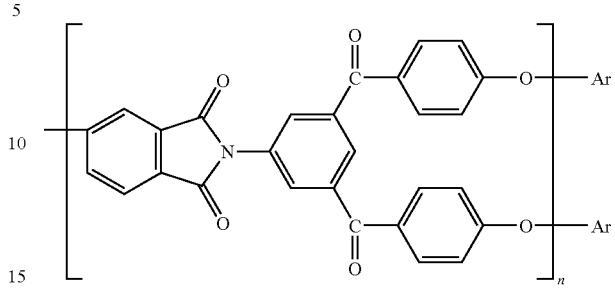

where the chain-end groups, Ar's, are 4-benzophenone with ortho-, meta- or para-ethynyl substituents in the 4'-position, and n=10-20.

DETAILED DESCRIPTION OF THE INVENTION

Aromatic polyimides (PIs) are well known, high-performance materials with widespread applications in the aerospace and electronics industries due to their excellent thermomechanical and dielectric properties. However, when fully imidized, most aromatic PI's have limited solubility in common organic solvents, thus restricting the choice in their processing options. Numerous research efforts have been focused on organo-soluble PIs from the modification of the structure without substantially decreasing rigidity of their backbone. Solubility is sought to allow processing polymers with preformed imide units and, many problems associated with handling poly(amic acid) (PAA) precursors can be avoided. In addition, homogeneous, post-polymer reactions of soluble aromatic polyimides would also allow better control in the introduction of desirable functional groups.

Another viable alternative to attaining solubility in aromatic PIs is to change the traditional, linear geometry of the macromolecules to three-dimensional, highly branched (dendritic) architecture. As a subset of dendritic polymers, hyperbranched polymers have several important advantages such as better solubility compare to their linear counterparts, and easier synthesis than their analogous dendrimers, which involve tedious multi-step synthesis. Large quantity of hyperbranched polymers can be easily produced from $AB_x$ ($x \geq 2$) monomers.

There have been only few reports on synthesis of hyperbranched PIs and their utilization. Thus, an objective of this invention was to provide the compositions of hyperbranched poly(ether-ketone-imide) with reactive acetylene chain-ends. Such reactive hyperbranched polymers may be useful as an additive to lower and stabilize melt-viscosity in the processing of high-temperature acetylene-based thermosets.

Acetylene-terminated (also known as ethynyl-terminated) imide oligomers are an important class of thermosetting resins for uses in computer circuit boards, as high-temperature polymer matrices in carbon-fiber composites, etc. They are generally prepared from appropriate ratios of (i) an aromatic amine such as para-phenylenediamine, meta-phenylenediamine, 4,4'-oxydianilne, 4,4'-methylenedianiline, etc.; (ii) an aromatic dianhydride such as 2,2'-bis(3,4-dicarboxyphenyl)hexafluoropropane dianhydride (6FDA), benzophenone-tetracarboxylic-3,3',4,4'-dianhydride, 4,4'-oxydiphthalic anhydride, biphenyl-3,3',4,4'-tetracarboxylic dianhydride, etc and (iii) ethynyl-containing endcapping agents such as 4-ethynylphthalic anhydride (4-PEPA), 3- or 4-ethynylaniline etc. These resins can be represented by the following generic structure:

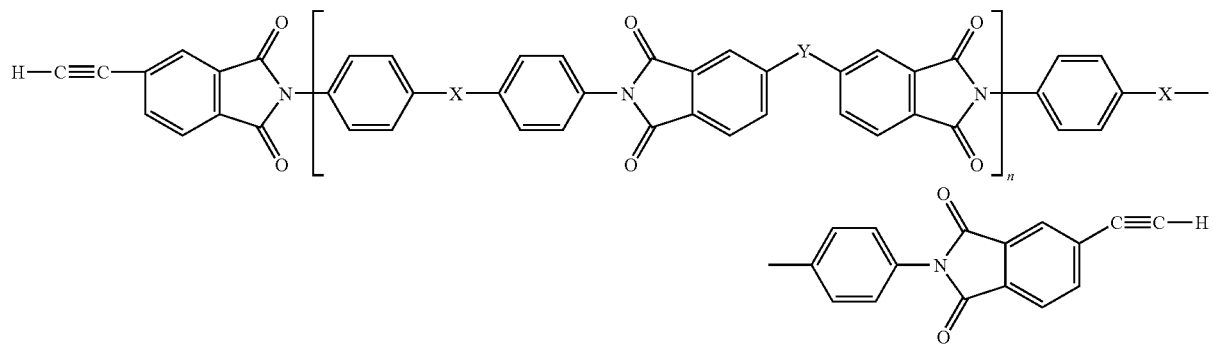

Where X=—CH$_2$—, —O—, —(CF$_3$)$_2$C—, Y=nil, —C(O)—, —(CF$_3$)$_2$C—, O, n=1-15

There are two key starting materials required for the synthesis of the subject ethynyl-terminated hyperbranched ether-ketone-imide polymers, namely (a) AB$_2$ monomer that can polymerize via a facile aromatic fluoride displacement reaction and (b) the endcapping agent that can undergo similar fluoride displacement reaction to allow a one-pot synthesis operation. Thus, ortho-, meta-, and para-bromobenzoyl chlorides (1) were heated with excess fluorobenzene (2) in presence of aluminum chloride to afford 4 (3 or 2)-bromo-4'-fluorobenzophenones (3), which were subsequently coupled with trimethylsilylacetylene (4) by the palladium-catalyzed reaction to afford 4-fluoro-4' (3' or 2')-trimethylsilylethynyl-benzophenone (5), followed by deprotection of the ethynyl group with cesium fluoride in methanol to yield 4-fluoro-4' (3' or 2')-ethynylbenzophenones (6).

Scheme 1:
Synthesis of 4-fluoro-4' (3' and 2')-ethynylbenzophenone
(i) AlCl$_3$, reflux; (ii) PdCl$_2$(PPh$_3$)$_2$, CuI, PPh$_3$, NEt$_3$.
(iii) CsF, MeOH.

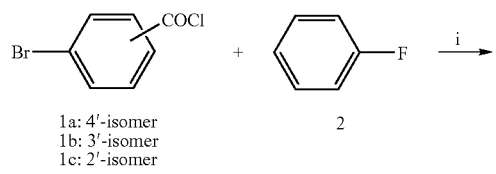

1a: 4'-isomer
1b: 3'-isomer
1c: 2'-isomer

2

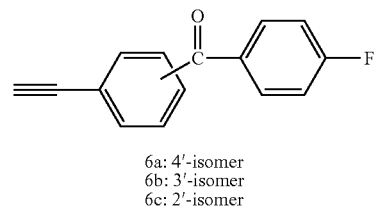

3a: 4-isomer
3b: 3-isomer
3c: 2-isomer

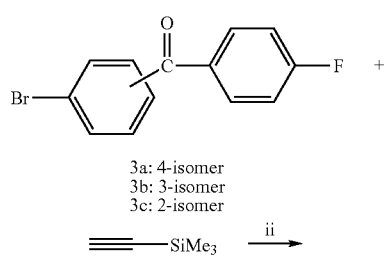

4

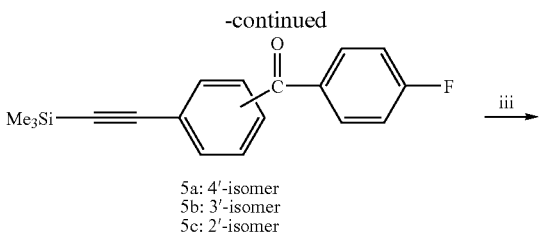

5a: 4'-isomer
5b: 3'-isomer
5c: 2'-isomer

6a: 4'-isomer
6b: 3'-isomer
6c: 2'-isomer

As shown in the following scheme, the AB$_2$ monomer, N-[3,5-bis(4-hydroxybenzoyl)benzene]-4-fluorophthalimide, (as described in U.S. Pat. No. 6,512,124, incorporated herein by reference) was self-polymerized in an N-methylpyrrolidinone (NMP)/toluene mixture in the presence of potassium carbonate to afford the hydroxyl-terminated poly(arylene-ether-ketone-imide) (HT-PAEKI) (Scheme 2). HT-PAEKI (7) was directly functionalized with 4-fluoro-4' (3' or 2')-ethynylbenzophenones to afford three acetylene (ethynyl) functionalized polymers (designated as p, m and o-AT-PAEKIs, 9a-c). After functionalization, the polymers were precipitated into 5% hydrochloric solution. The white solid were collected by filtration and Soxhlet-extracted with methanol to remove the residual NMP and unreacted endcapping agents. They were dried at 100° C. in vacuum oven for 48 hours before any characterization. The polymers were soluble in common organic solvents such as polar aprotic solvents (NMP, DMSO, DMF, DMAc etc), ether solvents (THF), and phenolic solvents (m-cresol, phenol). The intrinsic viscosity values of AT-PAEKIs ranged from 0.09 to 0.13 dL/g.

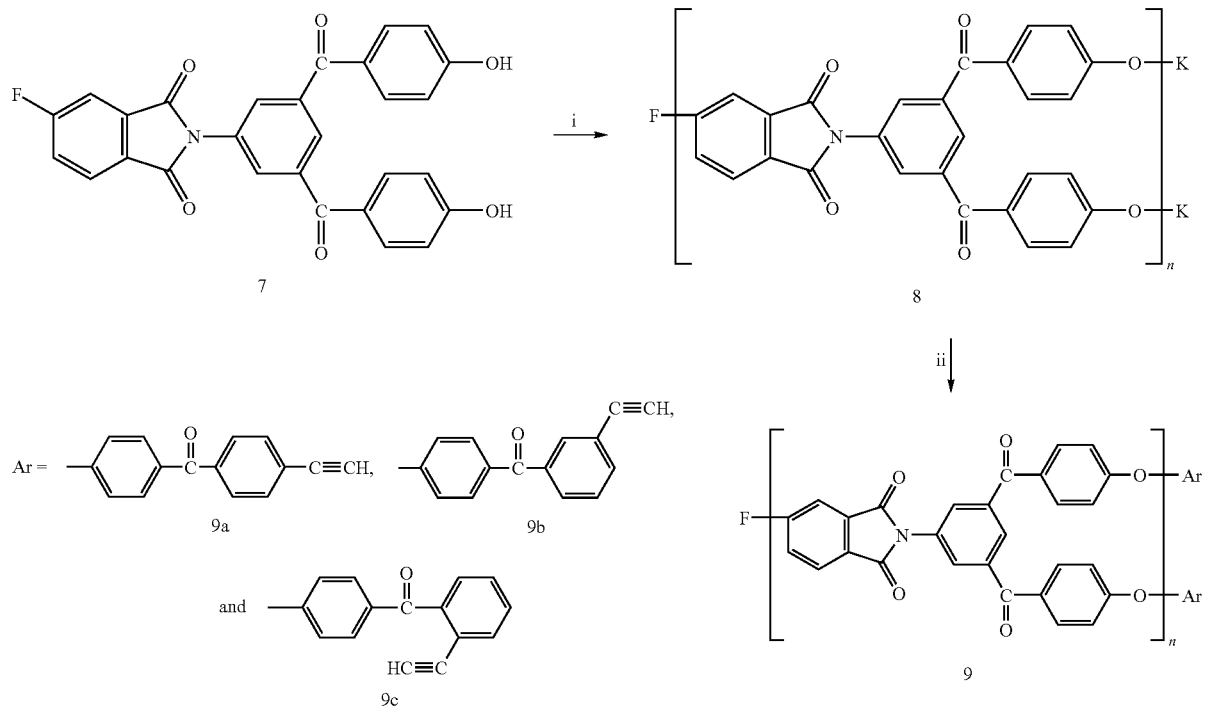

Scheme 2

All the hyperbranched polymers were characterized by differential scanning calorimetry (DSC) under $N_2$ atmosphere from room temperature up to 300° C. HT-PAEKI displayed a $T_g$ at 225° C. The $T_g$ value of p-AT-PAEKI was 168° C. while the $T_g$'s of m- and o-AT-PAEKIs were 159 and 154° C., respectively. p-AT-PAEKI displayed an exothermic peak at 264° C. while m-AT-PAEKI displayed an exothermic peak at 218° C. The exotherm of o-AT-PAEKI had the lowest-peak temperature at 208° C. p-AT-PAEKI exhibited an onset temperature of 204° C. and processing window of 36° C. On the other hand, m- and o-AT-PAEKIs displayed lower onset temperatures, 189 and 166° C., respectively. Both had narrower processing windows (30° C. for m-AT-PAEKI and 12° C. for o-AT-PAEKI) than p-AT-PAEKI. Compared with the phenylethynyl-terminated PAEKI,[3] AT-PAEKI displayed much lower exothermic peaks and narrower processing windows. Their 5% weight losses occurred at temperatures ranged from 471 to 491° C. in nitrogen and from 430 to 461° C. in air.

Hyperbranched polymers have a pseudo-globular structure with numerous terminating groups, which have more influence on the polymer properties, such as glass transition temperatures and solubility, than the two endgroups of the linear analogs. The meta and ortho units in linear polymers tend to decrease the $T_g$ because they disrupt the packing of polymer chains and create more free volume. In the case of hyperbranched polymers the linearity of terminating groups becomes less important since the hyperbranched structures have already disrupted the packing ability of terminating groups. The $T_g$'s are possibly influenced by the terminating group rotation. The linear endgroups, such as para-(ethynyl) benzophenone group, was able to rotate better than its non-linear (meta- and ortho) counterparts. This may explain that the $T_g$ of (para)4'PE-PAEKI was lower than those of 3'-(meta) and (ortho)2PE-PAEKI. 4'PE-PAEKI displayed an exotherm peak ($\Delta H_{exo}$=146 J/g) at 369° C. while 3'PE-PAEKI displayed an exotherm peak ($\Delta H_{exo}$=184 J/g) at 340° C. 2'PE-PAEKI exhibited a much lower-temperature exotherm peaked ($\Delta H_{exo}$=153 J/g) at 264° C. While the exact origin for the apparently enhanced thermal reactivity is still unclear, it is speculated that the intramolecular reactions or even intramolecular cyclizations might have happened at an elevated temperatures, resulting in a much lower exotherm peak. 4'PE-PAEKI exhibited an onset temperature of 276° C. and processing window of 109° C. On the other hand, 3' and 2'-PE-PAEKI's displayed lower onset temperatures, 211 and 198° C., respectively. Both had narrower processing windows (33° C. for 3'PE-PAEKI and 17° C. for 2'PE-PAEKI) than 4'PE-PAEKI. The 4'PE-PAEKI peak was narrow and symmetric while the 3'- and 2'PE-PAEKI peaks were broad and non-symmetric. After the first heating run no $T_g$s were observed for 4'- and 3'PE-PAEKIs. The crosslinking densities of both polymers were so high that their glass transition temperatures were possibly higher than 450° C., at which the polymers started to decompose. 2'PE-PAEKI exhibited a $T_g$ of 254° C. This seems to further support that 2'PE-PAEKI mostly underwent intramolecular reactions during the cure process, resulting in a lower crosslinking density, i.e., a lower $T_g$, than 4' and 3'-isomers after a heat treatment.

The following Examples illustrate the invention:

EXAMPLE 1

4-Bromo-4'-fluorobenzophenone (3a)

Into a 250 mL three-necked round-bottomed flask equipped with a magnetic stirrer and nitrogen inlet and outlet were added fluorobenzene (73.0 g, 0.760 mol) and 4-bromobenzoyl chloride (25.0 g, 0.114 mol). The mixture was then cooled to 0° C. and anhydrous aluminum chloride (17.6 g, 0.130 mol) was added in several portions. The mixture was stirred at room temperature for 30 min, heated to reflux for 4 hours and stirred at room temperature for 16 hours. The mixture was poured into 5% hydrochloric acid. The organic layer was diluted with methylene chloride and separated with the aid of a separatory funnel. Methylene chloride was removed under reduced pressure. The resulting white solid residue was dissolved in hot ethanol and allowed to cool to room temperature to give 27.0 g (85.0% yield) of white crystals, m.p. 108-109° C. FT-IR (KBr, cm$^{-1}$): 1647(carbonyl). Mass spectrum (m/e): 278, 280 (M$^+$). $^1$H-NMR (CDCl$_3$, δ in ppm): 7.12-7.18 (t, 2H, Ar—H), 7.62-7.83 (m, 6H, Ar—H). $^{13}$C-NMR (CDCl$_3$, δ in ppm): 115.42, 115.74, 127.49, 131.34, 131.63, 132.50, 132.61, 133.27, 133.33, 136.12, 163.54, 167.28, 193.98.

EXAMPLE 2

3-Bromo-4'-fluorobenzophenone (3b)

Into a 250 mL three-necked round-bottomed flask equipped with a magnetic stirrer and nitrogen inlet and outlet were added fluorobenzene (73.0 g, 0.760 mol) and 3-bromobenzoyl chloride (25.0 g, 0.114 mol). The mixture was then cooled to 0° C. and anhydrous aluminum chloride (17.6 g, 0.130 mol) was added in several portions. The mixture was stirred at room temperature for 30 min, heated to reflux for 4 hours and stirred at room temperature for 16 hours. The mixture was poured into 5% hydrochloric acid. The organic layer was diluted with methylene chloride and separated with the aid of a separatory funnel. Methylene chloride was removed under reduced pressure. The resulting white solid residue was dissolved in hot ethanol and allowed to cool to room temperature to give 28.4 g (89.0% yield) of white crystals, m.p. 84-85° C. FT-IR (KBr, cm$^{-1}$): 1648(carbonyl). Mass spectrum (m/e): 278, 280 (M$^+$). $^1$H-NMR (CDCl$_3$, δ in ppm): 7.14-7.21 (t, 2H, Ar—H), 7.34-7.40 (t, 1H, Ar—H), 7.66-7.73 (t, 2H, Ar—H), 7.81-7.90 (m, 3H, Ar—H). $^{13}$C-NMR (CDCl$_3$, δ in ppm): 115.53, 115.74, 122.65, 128.38, 129.96, 132.64, 132.75, 133.13, 133.35, 139.32, 163.71, 167.48, 193.63.

EXAMPLE 3

2-Bromo-4'-fluorobenzophenone (3c)

Into a 250 mL three-necked round-bottomed flask equipped with a magnetic stirrer and nitrogen inlet and outlet were added fluorobenzene (73.0 g, 0.760 mol) and 2-bromobenzoyl chloride (25.0 g, 0.114 mol). The mixture was then cooled to 0° C. and anhydrous aluminum chloride (17.6 g, 0.130 mol) was added in several portions. The mixture was stirred at room temperature for 30 min, heated to reflux for 4 hours and stirred at room temperature for 16 hours. The mixture was poured into 5% hydrochloric acid. The organic layer was diluted with methylene chloride and separated with the aid of a separatory funnel. Methylene chloride was removed under reduced pressure. The resulting white solid residue was dissolved in hot ethanol and allowed to cool to room temperature to give 27.4 g (86.0% yield) of white crystals, m.p. 51-53° C. FT-IR (KBr, cm$^{-1}$): 1648 (carbonyl). Mass spectrum (m/e): 278, 280 (M$^+$). $^1$H-NMR (CDCl$_3$, δ in ppm): 7.10-7.16 (t, 2H, Ar—H), 7.31-7.43 (m, 3H, Ar—H), 7.63-7.66 (dd, 1H, Ar—H), 7.81-7.86 (m, 2H, Ar—H). $^{13}$C-NMR (CDCl$_3$, δ in ppm): 115.74, 116.05, 119.39, 127.34, 128.87, 131.32, 132.66, 132.81, 132.96, 133.24, 140.39, 164.26, 168.03, 194.29.

EXAMPLE 4

4-Fluoro-4'-trimethylsilylethynylbenzophenone (5a)

Into a 250 mL three-necked round-bottomed flask equipped with a magnetic stirrer and nitrogen inlet and outlet were added 4-bromo-4'-fluorobenzophenone (10.0 g, 35.8 mmol), trimethylsilylacetylene (4.22 g, 43.0 mmol), triphenylphosphine (0.28 g), cuprous iodide (0.10 g), bis(triphenylphosphine) palladium dichloride (0.14 g) and 150 mL of triethylamine. The mixture was heated to reflux for 24 hours. The mixture was poured into 5% hydrochloric acid and the precipitate was collected by filtration. The resulting solid residue was recrystallized from heptane to afford 7.0 g (82% yield) of white crystals, m.p. 105-107° C. Anal. Calcd. for C$_{18}$H$_{17}$FOSi: C, 72.94%; H, 5.78%. Found: C, 73.47%; H, 5.91%. FT-IR (KBr, cm$^{-1}$): 3070, 2960, 2900 (CH$_3$), 2159 (ethynyl), 1645 (carbonyl) and 1249. Mass spectrum (m/e): 296 (M$^+$).

EXAMPLE 5

4-Fluoro-3'-trimethylsilylethynylbenzophenone (5b)

Into a 250 mL three-necked round-bottomed flask equipped with a magnetic stirrer and nitrogen inlet and outlet were added 3-bromo-4'-fluorobenzophenone (12.9 g, 46.3 mmol), trimethylsilylacetylene (5.00 g, 50.9 mmol), triphenylphosphine (0.28 g), cuprous iodide (0.10 g), bis(triphenylphosphine) palladium dichloride (0.14 g) and 150 mL of triethylamine. The mixture was heated to reflux for 24 hours. The mixture was poured into 5% hydrochloric acid and the precipitate was collected by filtration. The resulting solid residue was recrystallized from heptane to afford 13.0 g (95% yield) of yellow crystals, m.p. 63-65° C. Anal. Calcd. for C$_{18}$H$_{17}$FOSi: C, 72.94%; H, 5.78%. Found: C, 72.98%; H, 5.98%. FT-IR (KBr, cm$^{-1}$): 3070, 2960, 2900 (CH$_3$), 2160 (ethynyl), 1646 (carbonyl) and 1249. Mass spectrum (m/e): 296 (M$^+$).

EXAMPLE 6

4-Fluoro-2'-trimethylsilylethynylbenzophenone (5c)

Into a 250 mL three-necked round-bottomed flask equipped with a magnetic stirrer and nitrogen inlet and outlet were added 2-bromo-4'-fluorobenzophenone (11.0 g, 39.4 mmol), trimethylsilylacetylene (5.00 g, 50.9 mmol), triphenylphosphine (0.28 g), cuprous iodide (0.10 g), bis(triphenylphosphine)palladium dichloride (0.14 g) and 150 mL of triethylamine. The mixture was heated to reflux for 24 hours. The mixture was poured into 5% hydrochloric acid and the precipitate was collected by filtration. The resulting liquid was passed through a column (silica gel) using methylene chloride as the elution solvent to afford 7.82 g (67% yield) of a colorless liquid. Anal. Calcd. for C$_{18}$H$_{17}$FOSi: C, 72.94%; H, 5.78%. Found: C, 72.64%; H, 5.61%. FT-IR (KBr, cm$^{-1}$): 3070, 2960, 2900(CH$_3$), 2160 (ethynyl), 1646 (carbonyl) and 1249. Mass spectrum (m/e): 296 (M$^+$).

EXAMPLE 7

4-Fluoro-4'-ethynylbenzophenone (6a)

Into a 100 mL three-necked round-bottomed flask equipped with a magnetic stirrer and nitrogen inlet and outlet were added 5a (1.60 g, 5.40 mmol), cesium fluoride (1.64 g, 10.8 mmol) and methanol (25.0 mL). The mixture was stirred at room temperature for 2 hours. Then it was poured into water. The white solid collected by filtration was recrystallized from heptane to give 1.21 g (92.0% yield) of white crystals, m.p. 92-94° C. Anal. Calcd. for $C_{15}H_9FO$: C, 80.35%; H, 4.05%. Found: C, 80.30%; H, 4.09%. FT-IR (KBr, cm$^{-1}$): 3278, 3069, 2108 (ethynyl), 1651(carbonyl), 1600 and 1239. Mass spectrum (m/e): 224 (M$^+$). $^1$H-NMR (CDCl$_3$, δ in ppm): 3.26 (s, 1H, —C≡C—H), 7.13-7.20 (t, 2H, Ar—H), 7.58-7.61 (d, 2H, Ar—H), 7.72-7.75 (d, 2H, Ar—H) and 7.80-7.85 (m, 2H, Ar—H). $^{13}$C-NMR (CDCl$_3$, δ in ppm): 80.31, 82.64, 115.39, 115.70, 126.27, 129.73, 132.00, 132.52, 132.64, 133.36, 137.22, 163.56, 167.31, 194.32.

EXAMPLE 8

4-Fluoro-3'-ethynylbenzophenone (6b)

Into a 100 mL three-necked round-bottomed flask equipped with a magnetic stirrer and nitrogen inlet and outlet were added 5b (1.00 g, 3.37 mmol), cesium fluoride (1.02 g, 6.74 mmol) and methanol (20.0 mL). The mixture was stirred at room temperature for 2 hours. Then it was poured into water. The white solid collected by filtration was recrystallized from heptane to give 0.72 g (96.0% yield) of white crystals, m.p. 81-82° C. Anal. Calcd. for $C_{15}H_9FO$: C, 80.35%; H, 4.05%. Found: C, 80.06%; H, 4.19%. FT-IR (KBr, cm$^{-1}$): 3278, 3069, 2112 (ethynyl), 1651(carbonyl), 1600 and 1239. Mass spectrum (m/e): 224 (M$^+$). $^1$H-NMR (CDCl$_3$, δ in ppm): 3.15 (s, 1H, —C≡C—H), 7.13-7.19 (t, 2H, Ar—H), 7.42-7.48 (t, 1H, Ar—H) and 7.70-7.85 (m, 5H, Ar—H). $^{13}$C-NMR (CDCl$_3$, δ in ppm): 78.56, 82.50, 115.45, 115.76, 122.53, 128.52, 129.93, 132.61, 132.73, 133.24, 133.30, 135.72, 137.65, 163.62, 167.37, 194.18.

EXAMPLE 9

4-Fluoro-2'-ethynylbenzophenone (6c)

Into a 100 mL three-necked round-bottomed flask equipped with a magnetic stirrer and nitrogen inlet and outlet were added 5c (5.00 g, 16.9 mmol), cesium fluoride (5.10 g, 33.7 mmol) and methanol (100.0 mL). The mixture was stirred at room temperature for 2 hours. Then it was poured into water. The white solid collected by filtration was recrystallized from heptane to give 3.50 g (93.0% yield) of white crystals, m.p. 43-45° C. Anal. Calcd. for $C_{15}H_9FO$: C, 80.35%; H, 4.05%. Found: C, 80.12%; H, 4.11%. FT-IR (KBr, cm$^{-1}$): 3278, 3069, 2110 (ethynyl), 1651 (carbonyl), 1600 and 1239. Mass spectrum (m/e): 224 (M$^+$). $^1$H-NMR (CDCl$_3$, δ in ppm): 3.21 (s, 1H, —C≡C—H), 7.09-7.15 (t, 2H, Ar—H), 7.35-7.42 (m, 3H, Ar—H), 7.71-7.84 (m, 3H, Ar—H). $^{13}$C-NMR (CDCl$_3$, δ in ppm): 79.21, 82.54, 115.67, 115.98, 118.53, 128.02, 128.87, 132.63, 132.97, 132.96, 133.85, 140.79, 164.26, 168.08, 194.53.

EXAMPLE 10 p-Acetylene-terminated hyperbranched poly(arylene-ether-imide) (p-AT-PAEKI, 9a)

Into a 100 mL three-necked, round-bottomed flask equipped with a magnetic stirrer, nitrogen inlet and outlet, and Dean-Stark trap with a condenser, N-[3,5-bis(4-hydroxybenzoyl)benzene]-4-fluorophthalimide (1.0 g, 2.3 mmol), potassium carbonate (0.69 g, 5.0 mmol), and a mixture of NMP (60 mL) and toluene (30 mL) solvent were placed. The reaction mixture was then heated and maintained at 140-150° C. for 4 hours. During this time period, the water formed was removed by toluene azeotropic distillation via a Dean-Stark trap. After complete removal of toluene by an increased the flow of nitrogen, the orange solution was then heated at 160° C. for 3 hours. The solution became brown in color and viscous. Some precipitate was observed 30 min after reaction temperature had reached 160° C. The mixture was allowed to cool to 120° C. Then potassium carbonate (0.7 g, 5.0 mmol) and 4-fluoro-4'-ethynylbenzophenone (1.0 g, 4.5 mmol) were placed. The reaction mixture was then heated and maintained at 110-120° C. for 10 hours. After being allowed to cool down on its own, the mixture was poured into a beaker containing 5% hydrochloric acid (300 mL). The resulting precipitate was collected by suction filtration and air-dried. Off-white powder was dissolved in NMP again and passed through a cake of Celite 545 to remove any insoluble salts. The filtrate was poured in a beaker containing 5% hydrochloric acid (300 mL) and warmed up to around 60-70° C. for 2 hours. The white powder was collected and Soxhlet extracted with methanol for 24 hours. It was then dried under the reduced pressure over $P_2O_5$ at 100° C. for 48 hours. The yield was essentially quantitative. [η]=0.11 dL/g. Anal. Calcd. for $C_{43}H_{23}NO_7$: C, 77.58%; H, 3.49%; N, 2.10%. Found: C, 78.24%; H, 3.85%; N, 1.92%. FT-IR (KBr, cm$^{-1}$): 2110 (ethynyl). $^1$H-NMR (DMSO-d$_6$; δ in ppm): 3.16 (s, —C≡C—H), 7.16-8.39 (Ar—H).

EXAMPLE 11 m-Acetylene-terminated hyperbranched poly(arylene-ether-imide) (m-AT-PAEKI, 9b)

Compound 9b was synthesized from N[3,5-bis(4-hydroxybenzoyl)benzene]-4-fluorophthalimide (1.0 g, 2.3 mmol) and 4-fluoro-3'-ethynylbenzophenone (1.0 g, 4.5 mmol) using the same procedure for compound 9a to afford a quantitative yield. [η]=0.13 dL/g. Anal. Calcd. for $C_{43}H_{23}NO_7$: C, 77.58%; H, 3.49%; N, 2.10%. Found: C, 76.28%; H, 4.01%; N, 1.86%. FT-IR (KBr, cm$^{-1}$): 2112 (ethynyl). $^1$H-NMR (DMSO-d$_6$; δ in ppm): 3.34 (s, —C≡C—H), 7.14-8.39 (Ar—H).

EXAMPLE 12 o-Acetylene-terminated hyperbranched poly(arylene-ether-imide) (o-AT-PAEKI, 9c)

Compound 9c was synthesized from N-[3,5-bis(4-hydroxybenzoyl)benzene]-4-fluorophthalimide (1.0 g, 2.3 mmol) and 4-fluoro-3'-ethynylbenzophenone (1.0 g, 4.5 mmol) using the same procedure for compound 9a to afford a quantitative yield. [η]=0.09 dL/g. Anal. Calcd. for $C_{43}H_{23}NO_7$: C, 77.58%; H, 3.49%; N, 2.10%. Found: C, 76.79%; H, 3.74%; N, 1.98%. FT-IR (KBr, cm$^{-1}$): 2109 (ethynyl). $^1$H-NMR (DMSO-d$_6$; δ in ppm): 3.21 (s, —C≡C—H), 7.10-8.39 (Ar—H).

Thermal Properties of AT-PAEKI for Examples 10-12

| PAEK I | $T_g{}^a$ (°C.) | DSC Exotherm | | TGA | |
|---|---|---|---|---|---|
| | | Onset (°C.) | Peak (°C.) | in $N_2$ $T_{5\%}{}^b$ (°C.) | in air $T_{5\%}{}^b$ (°C.) |
| 9a | 168 | 204 | 264 | 491 | 461 |
| 9b | 159 | 189 | 218 | 471 | 457 |
| 9c | 154 | 166 | 208 | 475 | 430 |

$^a$Inflection in baseline on DSC thermogram obtained in $N_2$ with a heating rate of 10° C./min.
$^b$Temperature at which 5% weight loss occurred on TGA thermogram obtained with a heating rate of 10° C./min.

Having thus described exemplary embodiments of the present invention, it should be noted by those skilled in the art that the disclosures herein are exemplary only and that alternatives, adaptations and modifications may be made within the scope of the present invention.

We claim:

1. A method for the preparation of the compound having the formula:

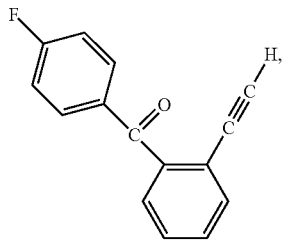

comprising the steps of:
a) heating a mixture of 4-bromobenzoyl chloride, fluorobenzene and anhydrous aluminum chloride and isolating 4-fluoro-2'-trimethylsilylethynylbenzophenone as the intermediate at the end of the reaction; and
b) stirring 4-fluoro-2'-trimethylsilylethynylbenzophenone, and cesium fluoride in methanol at room temperature to produce the compound.

2. A method for the preparation of the compound having the formula:

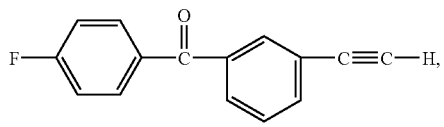

comprising the steps of:
a) heating a mixture of 4-bromobenzoyl chloride, fluorobenzene and anhydrous aluminum chloride and isolating 4-fluoro-3'-trimethylsilylethynylbenzophenone as the intermediate at the end of the reaction; and
b) stirring 4-fluoro-3'-trimethylsilylethynylbenzophenone and cesium fluoride in methanol at room temperature to produce the compound.

3. An ether-ketone-imide hyperbranched polymer having repeating units of the formula:

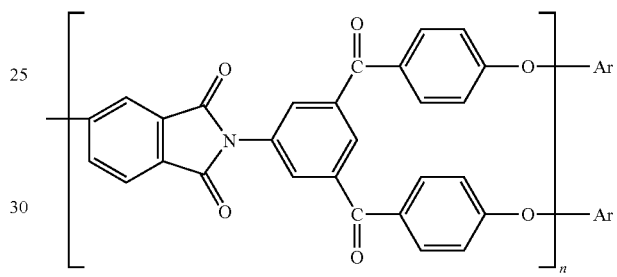

wherein n=10-20, and Ar is a 4-benzophenone with ortho-, para- or meta-ethynyl substituents in the 4'-position.

4. A method for synthesizing the polymer of claim 3 comprising:
a) heating N-[3,5-bis(4-hydroxybenzoyl)benzene]-4-fluorophthalimide in an N-methylpyrrolidinone/toluene mixture in the presence of potassium carbonate to form a hydroxyl-terminated poly(arylene-ether-ketone-imide); and
b) without isolation, directly functionalizing said hydroxyl-terminated poly(arylene-ether-ketone-imide) with 4-fluoro-2'-, 3'- or 4'-(ethynyl)benzophenone to produce the corresponding ethynyl terminated hyperbranched polymer.

* * * * *